US012728085B2

(12) United States Patent
Arredondo et al.

(10) Patent No.: US 12,728,085 B2
(45) **Date of Patent: *Sep. 8, 2026**

(54) N-ACYL AMINO ACID SURFACTANTS AND DERIVATIVES THEREOF

(71) Applicant: The Procter & Gamble Company, Cincinnati, OH (US)

(72) Inventors: Victor Manuel Arredondo, West Chester, OH (US); Karunakaran Narasimhan, Mason, OH (US); Howard David Hutton, III, Oregonia, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 639 days.

This patent is subject to a terminal disclaimer.

(21) Appl. No.: 17/835,025

(22) Filed: Jun. 8, 2022

(65) Prior Publication Data

US 2022/0401328 A1 Dec. 22, 2022

Related U.S. Application Data

(60) Provisional application No. 63/208,011, filed on Jun. 8, 2021.

(51) Int. Cl.

| | |
|---|---|
| ***C11D 1/10*** | (2006.01) |
| ***A61K 8/44*** | (2006.01) |
| ***A61Q 5/02*** | (2006.01) |
| ***A61Q 19/10*** | (2006.01) |
| ***C07C 233/47*** | (2006.01) |
| ***C11D 1/52*** | (2006.01) |
| ***C11D 3/33*** | (2006.01) |
| ***C11D 11/00*** | (2006.01) |
| ***C11D 17/00*** | (2006.01) |

(52) U.S. Cl.
CPC ................ *A61K 8/442* (2013.01); *A61Q 5/02* (2013.01); *A61Q 19/10* (2013.01); *C07C 233/47* (2013.01)

(58) Field of Classification Search
None
See application file for complete search history.

(56) References Cited

U.S. PATENT DOCUMENTS

| | | | | |
|---|---|---|---|---|
| 3,152,947 A * | 10/1964 | Monick | F26B 3/00 159/17.3 |
| 4,380,646 A | 4/1983 | Franzmann | |
| 5,496,959 A | 3/1996 | Day | |
| 5,856,538 A | 1/1999 | Strecker | |
| 6,028,042 A | 2/2000 | Chambers et al. | |
| 9,187,407 B2 * | 11/2015 | Koshti | C07C 303/26 |
| 10,988,713 B2 | 4/2021 | Schilling et al. | |
| 2003/0181341 A1 * | 9/2003 | Yoshimi | A61K 8/44 510/156 |
| 2010/0273879 A1 * | 10/2010 | Klug | A61Q 19/00 554/68 |
| 2013/0189212 A1 | 7/2013 | Jawale et al. | |
| 2014/0213665 A1 * | 7/2014 | Klug | A61K 8/046 562/574 |
| 2015/0126776 A1 | 5/2015 | Wang | |
| 2015/0141682 A1 * | 5/2015 | Koshti | C07C 51/60 554/37 |
| 2015/0250694 A1 | 9/2015 | Koshti et al. | |
| 2016/0152555 A1 * | 6/2016 | Wang | C07C 233/47 554/63 |
| 2024/0209282 A1 | 6/2024 | Arredondo | |

FOREIGN PATENT DOCUMENTS

| | | |
|---|---|---|
| CN | 102311359 A | 1/2012 |
| CN | 105802746 A | 7/2016 |
| CN | 106076192 A | 11/2016 |
| CN | 107382763 A | 11/2017 |
| CN | 108619027 A | 10/2018 |
| KR | 20180028207 A | 3/2018 |
| RU | 2657243 C2 | 6/2018 |
| WO | 9507881 A1 | 3/1995 |
| WO | 9507882 A1 | 3/1995 |
| WO | 9533030 A1 | 12/1995 |
| WO | 9741095 A1 | 11/1997 |
| WO | 2011130460 A1 | 10/2011 |
| WO | 2014008103 A1 | 1/2014 |
| WO | 2015026538 A1 | 2/2015 |
| WO | 2022117415 A1 | 6/2022 |

OTHER PUBLICATIONS

CN 106478466 A (Year: 2017).*

(Continued)

*Primary Examiner* — Lorna M Douyon
(74) *Attorney, Agent, or Firm* — Matthew J. Spegele

(57) ABSTRACT

Surfactant compositions and derivatives with low amounts of impurities are disclosed along with a method of making the same. A surfactant composition includes greater than 80% by weight of N-acyl amino acid surfactant of formula (I) and is substantially free of solvents and/or NaCl. A process for preparing an N-acyl amino acid surfactant includes combining an amino acid, a waterless base and a fatty alkyl ester of formula (III) to form a mixture that includes an amino acid salt of formula (II). The temperature of the mixture is increased to form a reaction mixture. Alkyl alcohol is removed from the reaction mixture, and the reaction mixture becomes substantially clear.

18 Claims, No Drawings

(56) References Cited

OTHER PUBLICATIONS

CN 107353223 A (Year: 2017).*
PCT Search Report and Written Opinion for PCT/US2022/072803 dated Aug. 26, 2022, 2020, 13 pages.
All Office Actions; U.S. Appl. No. 18/530,397, filed Dec. 6, 2023.
All Office Actions; U.S. Appl. No. 17/835,079, filed Jun. 8, 2022.
U.S. Appl. No. 17/835,079, filed Jun. 8, 2022, to Victor Manuel Arredondo et al.

* cited by examiner

N-ACYL AMINO ACID SURFACTANTS AND DERIVATIVES THEREOF

FIELD OF THE INVENTION

The present invention relates generally to N-acyl amino acid surfactants and derivatives and, in particular embodiments, N-acyl amino acid surfactant compositions with low amounts of impurities.

BACKGROUND OF THE INVENTION

Surfactants are the single most important cleaning ingredient in cleaning products. Environmental regulations, consumer habits, and consumer practices have forced new developments in the surfactant industry to produce lower cost, higher-performing, and environmentally friendly products.

Surfactants are key ingredients playing important roles in a variety of applications and consumer products such as in detergents, hard surface cleaners, fabric softeners, body wash, face wash, shampoo conditioners, conditioning shampoos, and other surfactant-based compositions. Many catalogs and patents describe surfactant options that can be too expensive to use. The high cost is many times due to the starting materials used to make such surfactants, inefficient reaction schemes and/or complex processes required for their manufacture to meet specific quality attributes. Accordingly, new methods are needed to produce surfactant compositions at low cost containing minimal impurities or additives.

N-acyl amino acid surfactants can be commercially manufactured from the corresponding fatty acid chlorides and amino acids using Schotten-Baumann chemistry as shown in equation 1.

equation 1

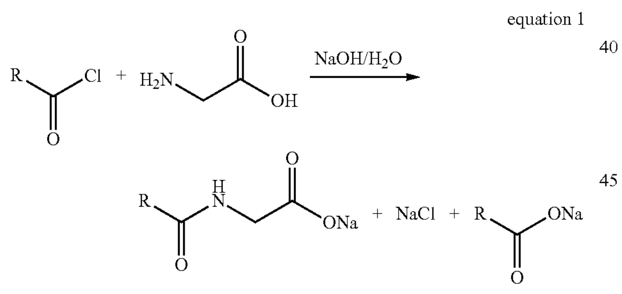

This amidation reaction is typically carried out in water, but the use of mixed water-solvent systems has been reported. Typically, the sodium N-acyl amino acid surfactant formed is obtained in the form of an aqueous composition containing 20-30% active with invariably high levels of undesirable inorganic salt (NaCl). The latter can be removed via additional post-reaction steps that can add significant cost and complexity. This surfactant making method is expensive and requires the manufacture of fatty acid chlorides which uses chlorinating agents such as phosphorous trichloride, ($PCl_3$), phosphorous pentachloride ($PCl_5$), thionyl chloride ($SOCl_2$), oxalyl chloride $(COCl)_2$ or phosgene (poisonous gas). These chlorinating agents are quite reactive, can be toxic, and might require very special handling and metallurgy. Also, depending on the specific chemistry and process used, separating the fatty acid chlorides away from byproducts and catalysts used has been difficult to solve. Thus, the products may contain undesired impurities that can be carried through to the synthesis of the corresponding surfactant.

One attempt to overcome these deficiencies is the synthesis of N-acyl glycinates and N-acyl alaninates by reacting corresponding amino acids with the fatty acid itself. The process generates highly colored (yellow) surfactant compositions containing relatively high levels of acylated di- and tri-peptide by-products with significant levels of unreacted fatty acid. Further, 100 to 200% mole excess of fatty acid is required for this process.

Fatty alkyl esters have also been used as starting materials. For example, methyl laurate can be reacted with the sodium salt of an amino acid and sodium methoxide in methanol in a pressurized reactor, with reaction pressures varied from 5-50 psig depending on the reaction temperature. Conversion to N-acyl sarcosinate from this reaction can be only 22%, while N-acyl alaninate conversion can be 67%. The N-acyl amino acid surfactant formed can be isolated by adding more methanol to the crude reaction mixture, then filtering it off and washing solid obtained with more methanol and finally drying isolated surfactant in the oven. The filtrate can be concentrated and analyzed to determine proportions of methyl laurate, and/or sodium salt of amino acid, and can be reused in the following batch. Hence, a further disadvantage of this approach is that it requires several process steps to isolate the reaction product.

In yet another conventional reaction, N-acyl amino acid surfactant is prepared using a polyol at 50-70 wt. % of the combined mass of the amino acid salt plus the methyl ester. However, the polyols used, glycerol and/or propylene glycol, remain in the final product mixture. Di-peptide impurities are found in the surfactant composition and the level varies depending on the level of polyol used in the reaction.

In summary, N-acyl amino acid surfactants made using these processes tend to contain high levels of undesirable by-products, such as salt (NaCl), di- and tri-peptide derivatives, or solvents such as methanol, glycerol and propylene glycol. Thus, there is a need for N-acyl amino acid surfactant compositions that are made under atmospheric conditions, are produced with low proportion of by-products and low levels of solvents or additives.

SUMMARY OF THE INVENTION

The present disclosure attempts to solve one more of the needs by providing a surfactant composition comprising greater than 80%, by weight, of an N-acyl amino acid surfactant of formula (I):

(I)

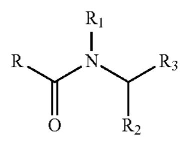

wherein R is an $C_5$-$C_{21}$ alkyl substituent, $R_1$ represents H, or $C_1$ to $C_4$ alkyl radical, $R_2$ represents H, $C_1$ to $C_4$ alkyl radical, or $C_1$ to $C_4$ hydroxyalkyl, $R_3$ represents the functional moiety COOM. M is a cationic group selected from the group consisting of alkali metal salts and hydrogen. The composition is substantially free of NaCl and solvents such as methanol and glycerol. The present disclosure also relates to surfactant compositions that are a solid or an aqueous liquid composition.

The present disclosure further relates to a process for preparation of an N-acyl amino acid surfactant which comprises combining an amino acid, a waterless base a fatty alkyl ester of formula (III):

(III)

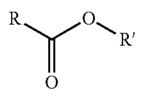

wherein R is selected from an $C_5$-$C_{21}$ alkyl substituent and R' is a $C_1$ or higher alkyl substituent, e.g. methyl, to form a mixture comprising an amino acid salt of formula (II)

(II)

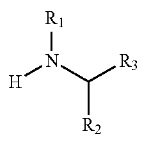

wherein $R_1$ represents H, or $C_1$ to $C_4$ alkyl radical, $R_2$ represents H, $C_1$ to $C_4$ alkyl radical or $C_1$ to $C_4$ hydroxyalkyl, $R_3$ represents COOM, M is a cationic group selected from alkali metal salts. The temperature of the mixture is increased up to about 180° C. or less, up to about 160° C. or less, or up to about 150° C. to form a reaction mixture. Alkyl alcohol is continuously removed from the reaction mixture, and the reaction mixture is allowed to become substantially clear.

In another aspect, the invention is directed to a consumer product cleaning or personal care composition comprising about 0.001 wt. % to about 99.999 wt. % or about 0.1 wt % to about 80 wt. % of N-acyl alaninate surfactant, as described herein, based on the total weight of the composition, and 0.001 wt. % to about 99.999 wt. % of one or more additional cleaning components, or one or more additional personal care components.

DETAILED DESCRIPTION OF THE INVENTION

Features and benefits of the present invention will become apparent from the following description, which includes examples intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.

As used herein, the articles including "the," "a" and "an" when used in a claim or in the specification, are understood to mean one or more of what is claimed or described.

As used herein, the terms "include," "includes" and "including" are meant to be non-limiting.

The term "substantially free of" or "substantially free from" as used herein refers to either the complete absence of an ingredient or a minimal amount thereof merely as impurity or unintended byproduct of another ingredient. A composition that is "substantially free" of/from a component means that the composition comprises less than about 0.5%, 0.25%, 0.1%, 0.05%, or 0.01%, or even 0%, by weight of the composition, of the component.

As used herein, the term "solid" includes granular, powder, flakes, noodles, needles, extrudates, ribbons, beads and pellets product forms and comprise less than about 0.5%, 0.25%, 0.1%, 0.05%, or 0.01%, or even 0%, by weight of the composition, of the water.

As used herein, "personal cleansing composition" includes personal cleansing products such as shampoos, conditioners, conditioning shampoos, shower gels, liquid hand cleansers, facial cleansers, and other surfactant-based liquid compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

In this description, all concentrations are on a weight basis of the composition, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

N-acyl Amino Acid Surfactant

The N-acyl amino acid surfactants disclosed herein have the following general formula (I):

(I)

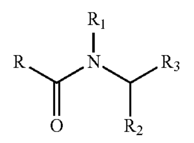

where R is an $C_5$-$C_{21}$ alkyl substituent, $R_1$ represents H, or $C_1$ to $C_4$ alkyl radical, $R_2$ represents H, $C_1$ to $C_4$ alkyl radical, or $C_1$ to $C_4$ hydroxyalkyl, $R_3$ represents COOM. M is a cationic group selected from the group consisting of alkali metal salts and hydrogen. Preferably, R is a $C_{7-17}$ alkyl substituent. The alkyl substituent may be branched or unbranched.

The N-acyl amino acid surfactants described herein are typically not single compounds as suggested by their general formula (I), but rather, as one skilled in the art would readily appreciate, they comprise a mixture of several homologs having varied chain lengths and molecular weight. The N-acyl amino acid surfactants described herein may be either saturated or unsaturated.

The N-acyl amino acid surfactant composition of the present invention comprises at least 50% by weight of sodium N-acyl amino acid surfactant. For example, the composition may comprise from 80-95% by weight of said N-acyl amino acid surfactant.

The N-acyl amino acid surfactant composition of the present invention further comprises fatty acid. The fatty acid may be present as free fatty acid or in the form of fatty acid soap. The amount in the composition may range from 1 to about 10% by weight, from 2 to 7% by weight, or from 3-5% by weight, specifically reciting all values within these ranges and any ranges created thereby.

Beneficially, the N-acyl amino acid surfactant composition of the present invention may be substantially free of impurities including water, salt (NaCl), polyol solvents, acylated di- and tri-peptide by-products, and methanol. The composition of the disclosure may comprise less than 5%, 2%, 1%, 0.1%, substantially free, and in some instances, free of one or any combination of these impurities.

The present disclosure further encompasses concentrated compositions, often referred to as pastes, and also solids, such as powders and tablets. These concentrated compositions may be combined with various adjunct ingredients (for example, water) to make a variety of detergent products, including personal cleansing compositions and laundry detergents.

Typically, inorganic salt (NaCl) is added to cleansing formulations made with sulfated surfactants to thicken the product. It has been surprisingly found that adding inorganic salt to the formulas that are substantially free of sulfated surfactants and/or using sulfate-free surfactants containing high inorganic salt in the presence of cationic conditioning polymer can cause product instability due to formation of a gel-like surfactant-polymer complex in the composition. Thus, it is desirable to avoid or minimize adding NaCl to the formula and/or use low inorganic salt (NaCl) containing raw materials. Commercially available sulfate-free surfactants such as sodium cocoyl alaninate, and other amino acid-based surfactants, typically come with high levels of inorganic salt such as 5% or higher. Use of these high salt (such as, NaCl) containing raw materials in sulfate-free surfactant-based cleaning formulations can cause formation of undesired gel-like surfactant-polymer complex in the product before use. The surfactant composition of the invention described herein can enable the formulation of stable cleansing products substantially free of sulfated surfactants.

Process of Making N-acyl Amino Acid Surfactants

The process described herein allows for the preparation of N-acyl amino acid surfactants having low levels of impurities. The conventional Schotten-Baumann acid chloride route to N-acyl amino acid surfactants—generates NaCl and other impurities, thereby yielding an undesirable output. Further, other reactions for making N-acyl amino acid surfactants use a low boiling point solvent and are carried out in closed reactors under pressure, and not under atmospheric conditions. High pressure reaction conditions are inherently more dangerous, time consuming, complicated and costly and are, therefore, not desirable. Others have used high boiling solvents such as polyols, glycerol and propylene glycol, to carry out reaction at atmospheric conditions, but the difficult-to-remove solvent stays with the surfactant.

A suitable method for preparing an N-acyl amino acid surfactants as disclosed herein includes the steps of: i) neutralizing an amino acid with a waterless base to form an amino acid salt of formula (II):

(II)

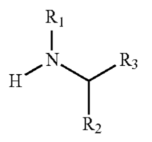

where $R_1$ represents H, or $C_1$ to $C_4$ alkyl radical, $R_2$ represents H, $C_1$ to $C_4$ alkyl radical or $C_1$ to $C_4$ hydroxyalkyl, $R_3$ represents COOM. M is a cationic group selected from alkali metal salts. The waterless base may comprise a $C_1$-$C_4$ alkoxide, e.g. sodium or potassium methoxide, and may be used in an amount within the range of 1.00 to 1.50 moles per mole of amino acid, 1.02 to 1.20 moles per mole of the amino acid or 1.05 to 1.10 moles per mole of the amino acid, specifically reciting all values within these ranges and any ranges created thereby.

The method for preparing an N-acyl amino acid surfactant further includes contacting the alanine salt of formula (II) with a fatty alkyl ester of formula (III):

(III)

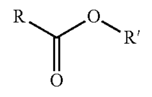

where R is selected from an C5-C21 alkyl substituent, and R' is a C1 or higher alkyl substituent, e.g. methyl. It is worth noting that the amino acid may be combined with the waterless base and the fatty alkyl ester in any order to form a mixture which comprises the salt of formula (II) above.

The method of preparing the N-acyl amino acid surfactant further comprises the steps of increasing the temperature of the mixture to 180° C., 160° C., or 150° C., to form a reaction mixture; continuously removing alkyl alcohol from the reaction mixture and allowing the reaction mixture to become substantially clear. For example, the temperature of the mixture can be from about 65° C. to about 180° C. or from about 90° C. to about 150° C., specifically reciting all values within these ranges and any ranges created thereby.

According to the present disclosure, the amino acid is a naturally occurring α-amino acid, the unnatural amino acid (opposite 'D' stereochemistry), or the racemic mixture. Suitable amino acids for use with the process of the present disclosure are selected from the group consisting of: alanine, sarcosine, glycine, serine, and proline. It is worth noting that combinations of the foregoing amino acids may be utilized. For example, a combination of alanine and glycine may be utilized.

Suitable waterless bases for use are those selected from the group consisting of alkali metals, such as sodium, lithium and potassium: alloys of two or more alkali metals, such as sodium-lithium and sodium-potassium alloys; alkali metal hydrides, such as sodium, lithium and potassium hydride; and alkali metal alkoxides, especially those containing from about one to about four carbon atoms such as sodium methoxide, potassium methoxide, lithium methoxide sodium ethoxide, potassium ethoxide, lithium ethoxide, sodium n-propoxide, potassium n-propoxide, sodium isopropoxide, potassium isopropoxide, sodium butoxide, potassium butoxide, sodium isobutoxide, potassium isobutoxide, sodium sec-butoxide, potassium sec-butoxide, and potassium tert-butoxide. Alkoxides are available in solid form or as solutions in the alcohol from which the alkoxide derives.

The relative molar amounts wherein the alkoxide is added to step i) in an amount within the range of 1.00 to 1.50 moles, 1.02 to 1.20 moles or 1.05 to 1.10 per mole of the amino acid, specifically reciting all values within these ranges and any ranges created thereby. The alkoxide not consumed in the neutralization catalyzes the reaction between amino acid salt and the fatty alkyl ester. Thus, in the process described herein the amount of alkoxide catalyst can range from 2 to 20 mole percent or from 5 to 10 mole percent, specifically reciting all values within these ranges and any ranges created thereby.

As used herein, the terms "fatty alkyl ester(s)" and "fatty acid esters" are intended to include any compound wherein the alcohol portion is easily removed, e.g. esters of volatile alcohols, $C_{1-4}$ alcohols (preferably methyl). Volatile alcohols are highly desirable. Methyl esters are the most highly preferred ester reactants. Suitable ester reactants can be prepared by the reaction of diazoalkanes and fatty acids or derived by alcoholysis from the fatty acids naturally occurring in fats and oils. Non-limiting examples are methyl octanoate (caprylate), methyl decanoate (caprate), methyl dodecanoate (laurate), methyl tetradecanoate (myristate), methyl hexadecanoate (palmitate), methyl octadecanoate (stearate), methyl oleate, ethyl dodecanoate (laurate), ethyl tetradecanoate (myristate), isopropyl dodecanoate (laurate), isopropyl tetradecanoate (myristate), and mixtures thereof. Suitable fatty acid esters can be derived from either synthetic or natural, saturated or unsaturated fatty acids. Non-limiting examples of saturated fatty acids include caprylic, capric, lauric, myristic, palmitic, and stearic. Mixtures of fatty acids derived from coconut oil, cottonseed oil, palm kernel oil, soybean oil, cotton seed oil, rapeseed oil, safflower oil, canola oil (low erucic acid), and corn oil and mixtures thereof. Most preferred is coconut oil.

It is preferred that the fatty alkyl esters be highly purified to remove color/odor materials, oxidation products, and their precursors. The free fatty acid level can be less than about 0.1% or less than about 0.05%, by weight of the esters. In addition, the fatty acid alkyl esters should have the lowest level of moisture possible, since any water present will react with the alkoxide catalyst, inhibit the amidation reaction and can lead to elevated levels of soap.

The molar ratio wherein the fatty alkyl ester is added to step ii) in an amount within the range of 0.90 to 1.50 moles per mole of amino acid, from 0.95 to 1.20 moles per mole of amino acid, or from 1.00 to 1.05 moles per mole of amino acid, specifically reciting all values within these ranges and any ranges created thereby. As shown in the examples, high active surfactant compositions with low levels of impurities are possible without further processing steps when the amino acid salt and the fatty alkyl ester are used in about equimolar amounts. Using an excess of fatty alkyl ester would result in a surfactant composition contaminated with unreacted fatty alkyl ester, thus requiring further processing for its removal. It is even less desirable to use the amino acid in excess since: (i) it is more expensive than the fatty alkyl ester, (ii) it does not have surface active properties and (iii) it would be difficult and costly to recover the unreacted amino acid salt from the surfactant mixture.

Surprisingly the reaction between the alanine salt of formula (II) and fatty alky ester of formula (III) can be performed at atmospheric or even under negative pressure while continuously distilling off alkyl alcohol (e.g. methanol) from the reaction mixture. The temperature conditions for the amidation reaction may range from about 65° C. to about 180° C. or from about 90° C. to about 150° C., specifically reciting all values within these ranges and any ranges created thereby. Reaction progress can be monitored by tracking the amount of alkyl alcohol collected and/or by quantitative $^{1}$H NMR, or other analytical techniques. The final N-acyl amino acid surfactant reaction mixture, made under these relatively mild conditions, is fluid at the amidation reaction temperature. The high active surfactant melt can be flaked, grinded, prilled, pelletized, and/or made into beads, noodles, needles, and ribbons by known methods to those skilled in the art.

The reaction may utilize an inert gas headspace to help reduce the level of oxygen available during the reaction. The reduced level of oxygen helps to reduce the amount of oxidation of the constituents of the reaction. Oxidation of the constituents can cause discoloration. A suitable example of an inert gas that may be utilized is nitrogen.

Additionally, the benefit of performing the reaction described herein at atmospheric or even negative pressure is that the resultant surfactant can be (if desired) substantially free of any solvents. Additionally, the alkyl alcohol, e.g. methanol, vapors can be condensed and recovered outside of the reactor. This collection of alkyl alcohol vapors can be re-used to make more methyl esters. The resultant surfactant can have less than about 5.0 wt % of fatty acid methyl ester, less than about 3.0 wt % or less than about 2.0 wt %, specifically reciting all values within these ranges and any ranges created thereby.

One of the advantages of the process of the invention it that the resultant N-acyl amino acid surfactant of formula (I) can be made to be substantially free of solvents, without using excesses of reactants, in high purity and without additional purifications steps.

In order to make a pumpable surfactant composition (pumpable at 50° C. or below), the active surfactant melt without any further purification may be diluted into water in an amount of from 20 to 70 wt. percent of the melt, and from about 25 to about 50 wt. percent of the melt. Alternatively, the water may be added to the high active surfactant melt at temperatures below 120° C. or under 100° C. under good mixing. The amount of water needed will depend on target surfactant active level, target viscosity and the solubility behavior of the surfactant. Examples 4 and 7 demonstrate making an aqueous, fluid surfactant composition by either directly adding water to the high active surfactant melt or by discharging surfactant from the reactor into another vessel with water and appropriate mixing equipment. The solid form of the surfactant—powder, flakes, pellets, beads, needles, noodles—may also be dissolved in water to make a pumpable surfactant composition for formulators to easily incorporate in cleaning formulations.

The process of the present disclosure minimizes the level of acylated di- and tri-peptide by-products and soap formed by using low catalyst loading, excluding water from the amidation reaction and by gradually increasing reaction temperature from 90° C. to about 150° C. Example 5 shows how higher level of undesirable soap, and other impurities are generated at higher temperatures and higher catalyst loading.

The process of the invention can be carried out as batch, semicontinuous, or in a continuous mode using suitable reactor(s) configurations. A conventional stirred-tank batch reactor equipped with a means for heating the reaction, a vapor column and condenser for collecting volatile alkyl alcohol, an efficient stirrer capable of stirring the reaction product mixture, a means for blanketing the reactor contents with nitrogen, and optionally a vacuum system capable of achieving a vacuum of less than 20 mm of Hg may be used to prepare the N-acyl amino acid surfactant composition disclosed herein.

Other reactors useful in the present invention is appropriately an apparatus with which liquid and solid mixtures of liquid and solid substances can be mixed using shear forces. In a static housing, the movement of the reaction mixture are brought about by internal mechanical stirring or mixing devices. The reaction apparatus can be a kneader or mixer equipped with sigma blades, masticator blades, or plough type agitator. Additional useful apparatuses include horizontal or vertical forced mixers equipped with mixing tools, for example sigma blades, masticator blades, plough type agitator, or throwing paddles, in combination with a cutting rotor.

Suitable horizontal forced mixers are those equipped with mixing tools or combinations of mixing tools such as, for example, sigma blades, masticator blades, or plough type agitator, in combination with a cutting rotor installed in the drum; more preferably horizontal forced mixers operating at a Froude number between 0.1 and 6, between 0.25 and 5 or between 0.4 and 4, and equipped with mixing tools, or combinations of mixing tools, such as, for example sigma blades, masticator blades and plough type agitator in combination with a cutting rotor installed in in the drum. Without wishing to be bound by theory, in the treatment of mixing processes, the Froude number, Fr, plays a major role. This dimensionless quantity is indicative of the relationship between the forces of inertia and gravity acting on a moving particle. The following equation is applicable here:

$$Fr = v^2/rg$$

where:
v=peripheral speed [m/s]
r=radius of mixing drum [m]
g=acceleration of gravity [m/s$^2$]

$$v = \pi \times D \times n/60$$

where:
D=diameter of mixing drum [m]
N=rotation rate of shaft [rpm]

The N-acyl amino acid surfactant composition and process for making described herein has a number of advantages over known commercial manufacturing processes and include:

1) High active surfactant composition substantially free of solvents and halide salts, like sodium chloride.
2) High conversion and yields can be achieved while avoiding laborious purification steps and concomitant product loss.
3) Fewer chemical engineering unit operations that can result in significant reduction in energy consumption.
4) Free of toxic and hazardous reagents, as described herein, and therefore the issue of handling these materials does not arise.
5) The resultant surfactant is substantially free of solvents that would need to be otherwise removed through additional post-reaction processing steps because they limit and/or impact the application and/or formulability of the surfactant.

Applications and Uses

In another aspect, the present disclosure is directed to a consumer product cleaning or personal care composition comprising about 0.001 wt. % to about 99.999 wt. % or about 0.1 wt % to about 80 wt. % of the N-acyl amino acid surfactants, e.g. alaninate, as described herein, based on the total weight of the composition, and 0.001 wt. % to about 99.999 wt. % of one or more additional cleaning components, or one or more additional personal care components.

In various embodiments, the at least one cleaning component is selected from the group consisting of a surfactant, an enzyme, a builder, an alkalinity system, an organic polymeric compound, a hueing dye, a bleaching compound, an alkanolamine, a soil suspension agent, an anti-redeposition agent, a corrosion inhibitor, and a mixture thereof. In some cases, the composition is selected from the group consisting of a granular detergent, a bar-form detergent, a liquid laundry detergent, a liquid hand dishwashing composition, a hard surface cleaner, a tablet, a disinfectant, an industrial cleaner, a highly compact liquid, a powder, and a decontaminant. In a class of cases, the composition is enclosed within a sachet or a multi compartment pouch comprising both solid and liquid compartments.

In some embodiments, the at least one personal care component is selected from the group consisting of an oil, and emollient, a moisturizer, a carrier, an extract, a vitamin, a mineral, an anti-aging compound, a surfactant, a solvent, a polymer, a preservative, an antimicrobial, a wax, a particle, a colorant, a dye, a fragrance, and mixtures thereof. In various cases, the composition is a shampoo, a hair conditioner, a hair treatment, a facial soap, a body wash, a body soap, a foam bath, a make-up remover, a skin care product, an acne control product, a deodorant, an antiperspirant, a shaving aid, a cosmetic, a depilatory, a fragrance, and a mixture thereof. In a class of cases, the composition is delivered in a form selected from the group consisting of a wipe, a cloth, a bar, a liquid, a powder, a creme, a lotion, a spray, an aerosol, a foam, a mousse, a serum, a capsule, a gel, an emulsion, a doe foot, a roll-on applicator, a stick, a sponge, an ointment, a paste, an emulsion spray, a tonic, a cosmetic, and mixtures thereof. In various embodiments, the composition further comprises a product selected from the group consisting of a device, an appliance, an applicator, an implement, a comb, a brush, a Substrate, and mixtures thereof. In some embodiments, the composition is dispensed from an article selected from the group consisting of a bottle, a jar, a tube, a sachet, a pouch, a container, a tattle, a vial, an ampoule, a compact, a wipe, and mixtures thereof.

EXAMPLES

Examples 1, 2, and 3 demonstrate the synthesis/preparation/manufacture of sodium N-acyl alaninate in greater than 85%, by weight, substantially free of solvent and sodium chloride (NaCl).

Analysis of the Reactions Conducted by a $^1$H NMR Method

In a scintillation vial reaction product and (internal standard, IS) were weighed out in a precision balance (0.1 mg readability). $D_2O$ (deuterium oxide) was added to the vial to fully dissolve sample and internal standard. The quantitative $^1$H NMR spectra were recorded at 600 MHz using standard $^1$H pulse sequence, pulse width of 12.00, 60 sec delay, and a 2.59 sec acquisition time. NMR data was processed using MestReNova 10.0.2. The integration of the peak at δ4.15 ppm for the methine (—CH—) group was used to calculate the wt. % of N-acyl alaninate surfactant. The integration of the triplet at δ2.16 ppm for the methylene (—$CH_2$—) adjacent to the carboxyl group was used to calculate the wt. % of fatty acid soap. The integration of the peak at δ3.30 ppm for the methine (—CH—) group was used to calculate the wt. % of unreacted alanine sodium salt. The integration of a singlet at δ3.65 ppm for the methyl ($CH_3$—) was used to calculate the wt. % of any residual fatty alkyl methyl ester. The integrations were compared to the integration region of the IS and used for the calculations. The wt. % of each species was calculated using the following equation:

$$\text{Wt. }\%(y)=\frac{A(y)}{A(IS)}\times\frac{n(IS)}{n(y)}\times\frac{MW(y)}{MW(IS)}\times\frac{W(IS)}{W(y)}\times P(IS)$$

Wt. % (y)=weight percent of "y" species in the sample
A=NMR integration
n=number of protons
MW=molecular weight
P=purity of the internal standard Example 1

A glass reactor vessel was used to carry out a series of experiments. It was fitted with a stirring rod with Teflon blade, a Dean-Stark trap equipped with a condenser, a nitrogen inlet, an addition funnel, and a thermocouple connected to a temperature control device. The reactor was heated by a heating mantle plugged into the temperature control device. The reactor was charged with L-alanine (108.0 g, 1.20 mol) and 25 wt. % sodium methoxide solution (286.57 g, 1.32 mol). The contents of reactor were heated to 65-68° C. under nitrogen and stirring. At this point CE1270 (265.86 g, 1.20)—a product of P&G Chemicals, methyl laurate/methyl myristate mixture—was added to the reactor (10-15 min) from the addition funnel while maintaining good mixing, and the temperature set to 90° C. Methanol evaporated was collected in the Dean-Stark. The temperature of the reaction was increased gradually to 120° C., after it reached 90° C. The initial two-phase reaction became one-phase during this time, and the reaction was considered complete when methanol stopped condensing, 2.5 h. The molten, fluid product was poured out of the reactor and cooled to ambient temperature. The composition of the clear, glassy product analyzed by quantitative $^{1}$H NMR (qNMR) was 89.1% sodium lauroyl/myristoyl alaninate, 5.9% fatty acid soap, 3.3% sodium alaninate, 1.0% methanol, and no residual methyl ester. HPLC-MS analysis showed less than 0.1% of di- and/or tri-alaninate by-products.

Example 2

A glass reactor vessel was fitted with a stirring rod with Teflon blade, a Dean-Stark trap equipped with a condenser, a nitrogen inlet, an addition funnel, and a thermocouple connected to a temperature control device. The reactor was heated by a heating mantle plugged into the temperature control device. The reactor was charged with L-alanine (108.0 g, 1.20 mol) and 25 wt. % sodium methoxide solution (280.0 g, 1.30 mol). The contents of reactor were heated to 65-68° C. under nitrogen and stirring. At this point methyl laurate (257.81 g, 1.20 mol) was added to the reactor (~30 min) from the addition funnel while maintaining good mixing, and the temperature set to 90° C. Methanol evaporated was collected in the Dean-Stark. The temperature of the reaction was increased gradually to 120° C., after it reached 90° C. The initial two-phase reaction became one-phase during this time. The reaction was considered complete when methanol stopped condensing, 4 h from the start of methyl ester addition. The molten, fluid product was poured out of the reactor and cooled to ambient temperature. The composition of the clear, glassy product analyzed by quantitative $^{1}$H NMR (qNMR) was 87.2% sodium lauroyl alaninate, 5.7% sodium laurate, 3.2% sodium alaninate, 1.1% methanol, and 0.6% methyl laurate. HPLC-MS analysis showed less than 0.1% of di- and/or tri-alaninate by-products.

Example 3

A glass reactor vessel was fitted with a stirring rod with Teflon blade, a Dean-Stark trap equipped with a condenser, a nitrogen inlet, an addition funnel, and a thermocouple connected to a temperature control device. The reactor was heated by a heating mantle plugged into the temperature control device. The reactor was charged with L-alanine (45.0 g, 0.50 mol) and 25 wt. % sodium methoxide solution (129.8 g, 0.60 mol). The contents of reactor were heated to 65-68° C. under nitrogen and stirring. At this point cocoyl methyl ester (119. g, 0.525 mol) was added to the reactor (10 min) from the addition funnel while maintaining good mixing, and the temperature set to 100° C. Methanol evaporated was collected in the Dean-Stark. The temperature of the reaction was increased gradually to 120° C., after it reached 100° C. The initial two-phase reaction became one-phase during this time. The reaction was considered complete when methanol stopped condensing. The molten, light-yellow, fluid product was poured out of the reactor and cooled to ambient temperature. The composition of the clear, glassy product analyzed by quantitative $^{1}$H NMR (qNMR) was 86.0% sodium cocoyl alaninate, 6.4% soap, 1.4% sodium alaninate. HPLC-MS analysis showed less than 0.1% of di- and/or tri-alaninate by-products.

Example 4

This example demonstrates the synthesis/preparation/manufacture of an aqueous solution of sodium N-acyl alaninate substantially free of sodium chloride (NaCl). A 2 liter glass reactor was fitted with a stirring rod with Teflon blade, a Dean-Stark trap equipped with a condenser, a nitrogen inlet, an addition funnel, and a thermocouple connected to a temperature control device. The reactor was heated by a heating mantle plugged into the temperature control device. The reactor was charged with L-alanine (100.9 g, 1.12 mol) and 25 wt. % sodium methoxide solution (279.3 g, 1.29 mol). The contents of reactor were heated to 65-68° C. under nitrogen and stirring. At this point methyl laurate (240.60 g, 1.12) was added to the reactor (10-15 min) from the addition funnel while maintaining good mixing, and the temperature set to 110° C. Methanol evaporated was collected in the Dean-Stark. The temperature of the reaction was increased gradually to 120° C., after it reached 110° C. Methanol was no longer condensing after about 2 hrs. Heat turned off, and the hot, molten, fluid product was cooled down to about 110° C. Deionized water (650.8 g) was added into the reactor with good mixing until product dissolved to form a clear, slightly yellow solution. The resultant solution at 60° C. was gently mixed until cooled to ambient temperature. The pH of the solution was adjusted from 13 to 10 with an appropriate acid solution. Analysis by quantitative $^{1}$H NMR showed it contained 22.9% sodium lauroyl alaninate, 1.5% fatty acid soap, 0.8% sodium alaninate, less than 0.5% of methanol, and no residual methyl laurate.

Example 5

This example demonstrates how higher level of undesirable soap, and other impurities are generated at higher temperatures and higher catalyst loading. A glass reactor vessel was fitted with a stirring rod with Teflon blade, a Dean-Stark trap equipped with a condenser, a nitrogen inlet, an addition funnel, and a thermocouple connected to a temperature control device. The reactor was heated by a heating mantle plugged into the temperature control device.

The reactor was charged with L-alanine (18.0 g, 0.20 mol) and 25 wt. % sodium methoxide solution (51.9 g, 0.24 mol). The contents of reactor were heated to 65-68° C. under nitrogen and stirring. At this point methyl laurate (47.4 g, 0.21 mol) was added to the reactor from the addition funnel while maintaining good mixing, and the temperature set to 150° C. Methanol evaporated was collected in the Dean-Stark. The reaction became clear and bubbly after reaching 150° C. in about 20 min. Reaction temperature was increased to 170° C. Reaction was terminated 30 min after, no more methanol was condensing. The clear, glassy product analyzed by quantitative $^{1}H$ NMR (qNMR) contained 71.0% sodium lauroyl alaninate, 11.8% sodium laurate, and 3.3% sodium alaninate. HPLC-MS showed the presence of a di-alaninate and N-methyl alaninate by-products in about 3.4% combined.

Example 6

In a horizontal forced mixer which has been equipped with plough type agitator, a distillation column and an inert gas inlet, sodium methoxide solution (1368.3 g, 6.4 mol) and solid L-alanine (532.8 g, 6.0 mol) were mixed at a temperature of 22-35° C. under nitrogen until a monophase liquid mixture formed. Coco fatty acid methyl ester (1283.8 g, 6.0 mol) was then added to the reactor, the temperature of the reaction mixture was gradually increased to 131° C., and the mixer was operated at a Froude number between 0.4 and 1 depending on the rheology of the composition. The alcohol from the base and alcohol formed during the reaction were removed by distillation from the forced mixer. The reaction was considered complete when methanol no longer was collecting. The molten product was discharged from the reactor and quickly cooled down to ambient temperature; 1255.8 g of light-yellow solid was obtained. Quantitative $^{1}H$ NMR (qNMR) analysis of the solid after grinding it gave the following composition: 88.7% sodium cocoyl alaninate, 4.2% soap, 2.7% sodium alaninate, 0.3% methanol, and 1.1% fatty acid methyl ester.

The resultant surfactant of the reaction described herein can be directly discharged into another vessel containing a solvent, e.g. water, to make a surfactant solution. Alternatively, the resulting surfactant can be discharged in solid form.

Example 7

In a horizontal forced mixer which has been equipped with plough type agitator, a distillation column and an inert gas inlet, sodium methoxide solution (1391.4 g, 6.5 mol) and solid L-alanine (543.8 g, 6.1 mol) were mixed at a temperature of 22-31° C. under nitrogen until a monophase liquid mixture formed. Coco fatty acid methyl ester (1293.1 g, 6.1 mol) was then added to the reactor, the temperature of the reaction mixture was increased gradually to 146° C., and the mixer was operated at a Froude number between 0.4 and 1.2 depending on the rheology of the composition. The alcohol from the base and alcohol formed during the reaction were removed by distillation from the forced mixer. The reaction was considered complete when methanol no longer was collecting. The molten product was directly discharged from the reactor into another vessel containing deionized water and equipped with an overhead mixer and impeller to make a surfactant solution. Quantitative $^{1}H$ NMR (qNMR) analysis of the surfactant solution obtained gave the following composition: 29.0% sodium cocoyl alaninate, 1.9% soap, 2.2% sodium alaninate, and 1.4% fatty acid methyl ester.

Example 8

In a horizontal forced mixer which has been equipped with plough type agitator, a distillation column and an inert gas inlet, sodium methoxide solution (1527.1 g, 7.2 mol) and solid L-alanine (597.1 g, 6.7 mol) were mixed at a temperature of 22-32° C. under nitrogen until a monophase liquid mixture formed. Coco fatty acid methyl ester (1428.6 g, 6.7 mol) was then added to the reactor, the temperature of the reaction mixture was increased gradually to 147° C., and the mixer was operated at a Froude number of 0.8. The alcohol from the base and alcohol formed during the reaction were removed by distillation from the forced mixer. The reaction was considered complete when methanol no longer was collecting. The molten product was directly discharged unto a cooled surface while spreading the fluid product into thin layers of various thicknesses. Quantitative $^{1}H$ NMR (qNMR) analysis of the surfactant solution obtained gave the following composition: 89.9% sodium cocoyl alaninate, 4.6% soap, 4.2% sodium alaninate, and 2.4% fatty acid methyl ester.

Example 9

In a 130-liter horizontal forced mixer equipped with plough type agitator, a distillation column with condensate receiver and an inert gas inlet, sodium methoxide solution (38.2 kg) and solid L-alanine (14.6 kg) were loaded and mixed at a Froude number of 0.8 and at a temperature of 22-32° C. under nitrogen for 20 minutes. Coco fatty acid methyl ester (35.0 kg) was then added to the reactor, the temperature of the reaction mixture was increased gradually to 140° C. The alcohol from the base and alcohol formed during the reaction were removed by distillation from the forced mixer. The reaction was considered complete when methanol no longer was collecting. The molten product was cooled to ambient temperature, and the solid product broken into particles of various sizes. Quantitative $^{1}H$ NMR (qNMR) analysis of the surfactant solution obtained gave the following composition: 94.8% sodium cocoyl alaninate, 3.4% soap, 1.8% sodium alaninate, and 0.1% fatty acid methyl ester.

Comparative Example 10

A 300 mL stainless-steel Parr reactor was charged with L-alanine (18.0 g, 0.20 mol), 25 wt. % sodium methoxide solution (49.5 g, 0.23 mol), methyl laurate (42.9 g, 0.20 mol), and additional methanol (9.7 g, ~40 wt. % based on the amount of charged starting materials). The reactor was sealed, stirrer set to 200 rpm, and heated to 85° C. for 4 h. The reactor was cooled down to about 40-45° C. and the pressure carefully released. The warm, reaction mixture contents poured into a glass baking sheet to evaporate solvent. The dry crude reaction product analyzed by quantitative 1H NMR and HPLC-HRMS: 27-29% sodium lauroyl alaninate, 25% methyl laurate, 10% sodium laurate soap, and significant levels of unreacted sodium alaninate.

Comparative Example 11

A 300 mL stainless-steel Parr reactor was charged methyl laurate (47.4 g, 0.21 mol), and a methanolic solution of sodium alaninate separately made by mixing L-alanine (18.0 g, 0.20 mol), 25 wt. % sodium methoxide solution (51.8 g, 0.24 mol). The reactor was sealed, stirrer set to 200 rpm, and heated to 90° C. for 4 h 10 min. The reactor was cooled down to about 40-45° C. and the pressure carefully released. The warm, reaction mixture contents poured into a glass baking sheet to evaporate solvent. A dry sample of the crude reaction product was analyzed by quantitative 1H NMR: 44.3% sodium lauroyl alaninate, 19.1% methyl laurate, 14.2% sodium laurate soap, and significant levels of unreacted sodium alaninate.

Examples 12 through 15 demonstrate the scope to synthesize/prepare/manufacture other sodium N-acyl amino acid surfactants in greater than 85%, by weight, substantially free of solvent and sodium chloride (NaCl) via this process.

Examples 12 & 13

The experiments were executed using starting materials and conditions identical to Example 1, except L-alanine was replaced by sarcosine and glycine, respectively.

TABLE 1

| | Example | |
|---|---|---|
| | 12[a] | 13[b,c] |
| Amino acid reactant | sarcosine | glycine |
| Catalyst load, mol % | 7 | 7 |
| Fatty acid methyl ester | methyl laurate | CE1270 |
| Surfactant, wt. % | 89.7 | 91.2 |
| Fatty acid soap, wt. % | 5.3 | 4.7 |
| Sodium salt of amino acid, wt. % | 1.1 | 2.4 |
| Methanol, wt. % | 0.2 | 0.0 |
| Pt-Co (APHA) color[d] | 105 (30% active aq. sol.) | 68 (23% active aq. sol.) |

[a]reaction product contained 1.5% of residual fatty acid methyl ester.
[b]reaction product was no longer fluid and mixing properly at the end of the reaction.
[c]reaction product contained 1.7% of residual fatty acid methyl ester.
[d]reaction product dissolved in water, Lovibond automated spectro-colorimeter (PFX-i series), 100-mm cell path.

Example 14: Sodium Lauroyl Serinate

A glass reactor vessel was fitted with a stirring rod with Teflon blade, a Dean-Stark trap equipped with a condenser, a nitrogen inlet, an addition funnel, and a thermocouple connected to a temperature control device. The reactor was heated by a heating mantle plugged into the temperature control device. The reactor was charged with L-serine (20.2 g, 0.19 mol) and 25 wt. % sodium methoxide solution (45.2 g, 0.21 mol). The contents of reactor were heated under nitrogen and stirring until the L-serine had reacted forming a clear solution. At this point methyl laurate (40.7 g, 0.19 mol) was added to the reactor from the addition funnel while maintaining good mixing, and the temperature set to 100° C. Methanol evaporated was collected in the Dean-Stark. The reaction was considered complete when methanol stopped condensing. The composition of the reaction product analyzed by quantitative $^{1}$H NMR (qNMR) was 89.2% sodium lauroyl serinate, 3.2% soap, 1.6% sodium serinate, 0.9% methyl laurate and <0.5% methanol.

Example 15: Sodium Lauroyl Prolinate

A glass reactor vessel was fitted with a stirring rod with Teflon blade, a Dean-Stark trap equipped with a condenser, a nitrogen inlet, an addition funnel, and a thermocouple connected to a temperature control device. The reactor was heated by a heating mantle plugged into the temperature control device. The reactor was charged with L-proline (20.1 g, 0.17 mol) and 25 wt. % sodium methoxide solution (41.40 g, 0.19 mol). The contents of reactor were heated to 65-68° C. under nitrogen and stirring. At this point methyl laurate (37.2 g, 0.17 mol) was added to the reactor from the addition funnel while maintaining good mixing, and the temperature set to 100° C. Methanol evaporated was collected in the Dean-Stark. The temperature of the reaction was increased gradually to 128° C., after it reached 100° C. The initial two-phase reaction became one-phase during this time. The reaction was considered complete when methanol stopped condensing. The molten, light-yellow, fluid product was poured out of the reactor and cooled to ambient temperature. The composition of the clear, glassy product analyzed by quantitative 1H NMR (qNMR) was 88.4% sodium lauroyl prolinate, 1.7% sodium prolinate. Soap level unknown, peaks overlapping with prolinate surfactant ring peaks. Methyl laurate not detected.

Example 16

This example demonstrates the synthesis/preparation/manufacture of a fluid surfactant blend of consisting of sodium N-acyl alaninate/N-acyl glycinate in greater than 85%, by weight, substantially free of solvent and sodium chloride (NaCl).

A glass reactor vessel was fitted with a stirring rod with Teflon blade, a Dean-Stark trap equipped with a condenser, a nitrogen inlet, an addition funnel, and a thermocouple connected to a temperature control device. The reactor was heated by a heating mantle plugged into the temperature control device. The reactor was charged with L-alanine (89.1 g, 1.00 mol), glycine (26.3 g, 0.35 mol) and 25 wt. % sodium methoxide solution (320.0 g, 1.49 mol). The contents of reactor were heated to 68° C. under nitrogen and stirring. At this point CE1270 (299.0 g, 1.35 mol)—a product of P&G Chemicals, methyl laurate/methyl myristate mixture—was added to the reactor (~45 min) from the addition funnel while maintaining good mixing, and the temperature set to 90° C. Methanol evaporated was collected in the Dean-Stark. The temperature of the reaction was increased gradually to 125° C., after it reached 90° C. The initial two-phase reaction became one-phase during this time. The reaction was considered complete when methanol stopped condensing, 3.5 h from the start of methyl ester addition. The molten, light-yellow, fluid product was poured out of the reactor and cooled to ambient temperature. The composition of the glassy product analyzed by quantitative $^{1}$H NMR (qNMR) was 67.2% sodium lauroyl/myristoyl alaninate, 24.2% sodium lauroyl/myristoyl glycinate, 5.1% sodium soap, 2.4% sodium alaninate, 1.3% methanol and 0.1% methyl ester.

Examples 17-22

Examples 17-22 in Table 2 below show the ingredient lists for personal care products, e.g. shampoo, body wash and the like.

TABLE 2

| | Examples, active wt % | | | | | |
|---|---|---|---|---|---|---|
| Ingredients | 17 | 18 | 19 | 20 | 21 | 22 |
| Sodium Cocoyl Alaninate [1] | 5.0 | 14.22 | 4.0 | 2.5 | 4.0 | 10.0 |
| Disodium Laureth Sulfosuccinate [2] | 10.0 | — | — | — | — | — |
| Sodium Cocoyl Isethionate [3] | 5.0 | — | 6.0 | 6.0 | 6.0 | — |
| Lauramidopropyl Betaine [4] | 5.0 | — | 9.75 | — | 2.44 | — |
| Cocamidopropyl Betaine [5] | — | — | — | 9.75 | 7.31 | — |
| Coco-betaine[6] | — | — | — | — | — | 4.0 |
| Polyquaternium 10 [7] | 0.35 | — | — | — | — | — |
| Polyquaternium 10 [8] | — | — | 0.80 | — | — | — |
| Polyquaternium 10 [9] | — | — | — | — | — | 0.10 |
| Polyquaternium 6 [10] | 0.20 | — | — | 0.05 | 0.55 | — |
| Guar Hydroxypropyltrimonium Chloride [11] | — | 0.30 | — | — | — | — |
| Guar Hydroxypropyltrimonium Chloride [12] | — | — | — | — | — | 0.40 |
| Tetrasodium EDTA [13] | 0.16 | — | 0.16 | 0.16 | 0.16 | 0.16 |
| Sodium Benzoate [14] | 0.25 | 0.25 | 0.25 | 0.25 | 0.25 | 0.25 |
| Sodium Salicylate [15] | — | — | 0.50 | — | 0.25 | — |
| Methylchloroisothiazolinone and Methylisothiazolinone [16] | 0.0005 | 0.0005 | — | 0.0005 | — | 0.0005 |
| Perfume | 2.0 | 0.90 | 1.1 | 0.85 | 1.2 | 1.0 |
| Citric Acid [17] | to pH 6.0 | to pH 6.0 | to pH 5.5 | to pH 6.0 | to pH 5.5 | to pH 6.0 |
| Water | Q.S. | Q.S. | Q.S. | Q.S. | Q.S. | Q.S. |

[1] Sodium Cocoyl Alaninate made according to the present disclosure.
[2] Chemccinate DSLS from Lubrizol
[3] Jordapon CI Prill from BASF
[4] Mackam DAB ULS from Solvay
[5] Amphosol HCA-HP from Stepan
[6] Dehyton AB 30 from BASF
[7] UCARE Polymer JR-30M from Dow
[8] UCARE Polymer LR-30M from Dow
[9] UCARE Polymer KG-30M from Dow
[10] Flocare C 106 MSS available from SNF
[11] Jaguar C500 from Solvay
[12] Jaguar Excel from Solvay
[13] Versene 220 from Dow
[14] Sodium benzoate from Emerald Kalama Chemical
[15] Sodium salicylate from JQC (Huayin) Pharmaceutical
[16] Kathon CG from Dow
[17] Citric acid from ADM Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A surfactant composition comprising greater than 80%, by weight, of an N-acyl amino acid surfactant of formula (I):

(I)

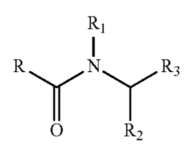

wherein R is an $C_5$-$C_{21}$ alkyl substituent and $R_1$ represents H, $R_2$ represents H, $C_1$ to $C_4$ alkyl radical or $C_1$ to $C_4$ hydroxyalkyl, $R_3$ represents COOM, M is a cationic group selected from the group consisting of alkali metal salts, wherein the composition is substantially free of solvents and/or NaCl; wherein the surfactant comprises about 0.1 wt % to about 5.0 wt % of fatty acid methyl ester.

2. The composition of claim 1, wherein the alkyl substituent is either saturated or unsaturated and either branched or unbranched.

3. The composition of claim 1, wherein R is a C7-17 alkyl substituent.

4. The composition of claim 1, wherein the composition is substantially free of polyol solvents and water.

5. The composition of claim 1, wherein the composition comprises greater than 85%, by weight of the N-acyl amino acid surfactant.

6. The composition of claim 1, wherein the amino acid surfactant is selected from at least one of: N-acyl alaninate, N-acyl glycinate and N-acyl serinate.

7. The composition of claim 1, wherein the composition contains less than 2% by weight of an N-acyl amino acid dipeptide salt, a tri-peptide salts or a mixture thereof.

8. The composition of claim 1, wherein the composition comprises from 0 to less than 0.5% by weight of methanol.

9. The composition of claim 1, wherein the composition is a solid or in solution.

10. The composition of claim 1, wherein the composition is selected from the group consisting of a powder, granule, flake, noodle, needle, extrudate, ribbon, bead and pellet and mixtures thereof.

11. The composition of claim 1, wherein the composition is selected from a granular detergent, a bar-form detergent, a liquid laundry detergent, a gel detergent, a single-phase or multi-phase unit dose detergent, a detergent contained in a single-phase or multi-phase or multi-compartment water soluble pouch, a liquid hand dishwashing composition, a laundry pretreat product, a surfactant contained on or in a porous substrate or nonwoven sheet, an automatic dishwashing detergent, a hard surface cleaner, a fabric softener composition, a personal care composition and mixtures thereof.

12. A process for preparation of the surfactant composition according to claim 1 which comprises preparing the N-acyl amino acid surfactant comprising:

combining:

an amino acid, a waterless base, a fatty alkyl ester of formula (III)

(III)

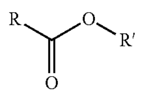

wherein R is an $C_5$-$C_{21}$ alkyl substituent, R' is a $C_{1-4}$ alkyl substituent, to form a mixture comprising an amino acid salt of formula (II)

(II)

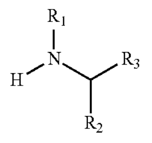

wherein $R_1$ represents H, or $C_1$ to $C_4$ alkyl radical, $R_2$ represents H, $C_1$ to $C_4$ alkyl radical or $C_1$ to $C_4$ hydroxyalkyl, $R_3$ represents COOM, Mis a cationic group selected from alkali metal salts;

increasing the temperature of the mixture up to about 180° C. to form a reaction mixture;

continuously removing alkyl alcohol from the reaction mixture; and allowing the reaction mixture to become clear.

13. The process of claim 12, wherein the step of increasing the temperature of the mixture comprises increasing the temperature of the mixture from about 65° C. to about 180° C.

14. The process of claim 12, wherein allowing the reaction mixture to become clear comprises allowing the reaction mixture to go from two phases to a single phase and the process is performed at atmospheric pressure under an inert gas headspace.

15. The process of claim 12, wherein the amino acid comprises a naturally occurring α-amino acid, an unnatural amino acid, or a racemic mixture selected from the group consisting of alanine, sarcosine, glycine, and serine; and the waterless base comprises a $C_1$-$C_4$ alkoxide in methanol solution, or combinations thereof.

16. The process of claim 12, wherein the mixture comprises from 1.00 to 1.50 moles of the waterless base per mole of the amino acid.

17. The process of claim 12, wherein the mixture comprises from 0.90 to 1.50 moles of the fatty alkyl ester per mole of the amino acid.

18. The process of claim 12, wherein the concentration of N-acyl amino acid surfactant in the reaction mixture is greater than 85% by weight.

* * * * *